United States Patent [19]

Zimmerman

[11] Patent Number: 5,055,557

[45] Date of Patent: Oct. 8, 1991

[54] ULTRAPURIFICATION OF FACTOR IX AND OTHER VITAMIN K-DEPENDENT PROTEINS

[75] Inventor: Theodore S. Zimmerman, La Jolla, Calif.

[73] Assignee: Scripps Clinic & Research Foundation, La Jolla, Calif.

[21] Appl. No.: 275,466

[22] Filed: Nov. 23, 1988

Related U.S. Application Data

[63] Continuation of Ser. No. 910,315, Sep. 2, 1986, which is a continuation of Ser. No. 800,902, Nov. 22, 1985, abandoned, which is a continuation of Ser. No. 707,179, Mar. 1, 1985, abandoned, which is a continuation of Ser. No. 472,413, Mar. 4, 1983, abandoned.

[51] Int. Cl.$^5$ ............................ C07K 3/20; C07K 3/28
[52] U.S. Cl. .................................... 530/381; 530/380; 530/384; 530/413; 530/830; 435/183; 435/184
[58] Field of Search ............... 530/381, 384, 380, 413, 530/830; 425/183, 184

[56] References Cited

U.S. PATENT DOCUMENTS

| | | | |
|---|---|---|---|
| 3,560,475 | 2/1971 | Fekete et al. | 260/112 B |
| 3,920,625 | 11/1975 | Andersson et al. | 260/112 B |
| 4,081,432 | 3/1978 | Delente et al. | 260/112 B |
| 4,361,509 | 11/1982 | Zimmerman et al. | 260/112 B |
| 4,411,794 | 10/1983 | Schwinn et al. | 260/112 B |

OTHER PUBLICATIONS

J. Biol. Chem., 255:4980–4983 (1980), Brown et al.
J. Biol. Chem., 253:5946–5951 (1978), Osterud et al.
Methods in Enzymology, 80:221–228 (1982), Miletich et al.
Goodall et al, "Affinity Depletion and Affinity Purification of Human Factor IX by Monoclonal Antibodies", Protides of the Biological Fluids, Proceedings of the 13th Colloquium, vol. 30, Feb. 1983, pp. 403–407, Pergamon Press, Oxford (Great Britain).
Vehar et al., Nature, 312, 337–342 (1984).
Proteins, Creighton, W. H. Freeman Co., New York (1983), 78–79.
F. Rotblat et al., "Preparation of Factor IX–Deficient Human Plasma . . . ", Thrombosis and Haemostasis, 46, (1) 1–478 (Jul. 12, 1981) (Abstract No. 1055, p. 339).
A. Goodall et al., "Preparation of Factor IX Deficient Human Plasma . . . ", Blood, vol. 59, No. 3 (Mar. 1982), pp. 664–670.

*Primary Examiner*—Howard E. Schain
*Attorney, Agent, or Firm*—Morgan & Finnegan

[57] ABSTRACT

A method of recovering active, highly purified and concentrated vitamin K-dependent proteins from plasma, concentrate or mixtures of proteins produced by recombinant DNA technology using an immuno adsorbent comprising a monoclonal antibody.

13 Claims, No Drawings

ULTRAPURIFICATION OF FACTOR IX AND OTHER VITAMIN K-DEPENDENT PROTEINS

This is a continuation of co-pending application Ser. No. 910,315, filed on Sept. 2, 1986, which in turn is a continuation of U.S. Pat. Ser. No. 800,902, filed on Nov. 22, 1985, now abandoned, which in turn is a continuation of U.S. Pat. Ser. No. 707,179 filed on Mar. 1, 1985, now abandoned and which in turn is a continuation of U.S. Pat. Ser. No. 472,413, filed on Mar. 4, 1983, now abandoned.

BACKGROUND OF THE INVENTION

1. Field of the Invention

This invention relates generally to a method of separating and purifying Factor IX and other vitamin K-dependent proteins including Factor II, Factor VII, Factor X, prothrombin, Protein C, and Protein S. More specifically, high purity protein is separated by a chromatographic adsorption and concentration technique from plasma or concentrate.

2. Description of the Prior Art

Blood coagulation factors play a vital role in the normal coagulation mechanism. For instance, patients with a deficiency of Factor IX exhibit severe bleeding problems ("Hemophilia B"). It would be desirable to be able to isolate substantial quantities of Factor IX and other vitamin K-dependent proteins for therapeutic administration, as well as for scientific study, and several processes directed to this objective have been described in the literature. The process of the present invention surpasses these processes in providing a combination of high yield of the desired protein with high purity, and particularly with relatively low contamination by other clotting factors. In addition, the prior art processes require a large number of steps each of which is time-consuming and introduces losses of protein into the overall process.

One such process is that of S. P. Bajaj, et al., "A Simplified Procedure for Purification of Human Prothrombin, Factor IX and Factor X", in Preparative Biochemistry, 11 (4), 397–412 (1981). This process subjects pooled plasma to adsorption onto and elution from barium citrate, ammonium sulfate fractionation, DEAE-Sephadex chromatography, and heparin-agarose chromatography in a sodium citrate buffer at pH 7.5, to separate prothrombin, Factor X, and Factor IX. The reported yield of Factor IX was about 35%, at a specific activity of 80–220 units/mg. Another process is that of J. P. Miletich, et al., "Purification of Human Coagulation Factors II, IX, and X Using Sulfated Dextran Beads", in Methods in Enzymology, Vol. 80, pp. 221–228. Fresh frozen plasma is thawed, and subjected to a sequence of precipitation with barium citrate, resuspension in Tris-HCl with diisopropylfluorophosphate, precipitation with ammonium sulfate, chromatography on De-52 cellulose, and application of selected pooled fractions to sulfated dextran beads. Following concentration, the fraction containing the Factor IX is said to be contaminated with as much as 1 wt. % of Factor X. B. Osterud, et al. in "Human Blood Coagulation Factor IX", J. Biological Chemistry, Vol. 253, No. 17, pp. 5946–5951 (1978), describe the purification of Factor IX by a sequence of adsorption onto and elution from barium sulfate, DEAE-cellulose batch chromatography, polyacrylamide gel electrophoresis, and heparin-agarose affinity chromatography. The Factor IX activity was said to be 207 units/mg, though the yield of Factor IX was not started.

Hence, it is clear that there still exists a need for an improved method for separating and purifying Factor IX or other vitamin K-dependent proteins from plasma or concentrates. Therefore, it is an object of the present invention to satisfy such a need.

SUMMARY OF THE INVENTION

The present invention relates to a method of separation of a Vitamin K-dependent protein from source material containing the desired protein and one or more other proteins. The method achieves the object of producing a highly purified protein using an adsorption procedure employing monospecific antibodies to the protein.

The first step involves immunoadsorption of the protein from a source material, such as plasma or a concentrate. The adsorbent employed comprises a monoclonal antibody specific to the protein, which is bound to a suitable substrate, such as agarose beads. After the protein is initially adsorbed, the substrate particles are washed extensively with a buffer solution to remove unadsorbed protein. The adsorbed material is then treated with a solution to elute the adsorbed protein. The protein as recovered is highly purified, i.e., largely free from contaminants, and can be employed therapeutically or can be further purified.

The process of the present invention provides Factor IX in purification on the order of 1500-fold, which represents a significant improvement over prior procedures, while providing a specific activity of about 34.8 units/mg or higher. Furthermore, the yields of Factor IX is this novel process average about 50%, and can be as high as about 70%.

The process is readily adaptable to recovering in purified form any of the proteins known as Vitamin K-dependent proteins, including Factor II, Factor VII, Factor IX, Factor X, prothrombin, Protein C, or Protein S. Typical sources include plasma, plasma fractions, and plasma concentrates. The protein can also be purified from a mixture of proteins produced by recombinant DNA technology, that is, a mixture of proteins expressed by bacteria, yeast, or other cells into which a gene for producing the protein of interest has been inserted. The technique for such gene insertion is known to those of ordinary skill in this art, who also recognize that the expressed protein of interest is usually in a mixture with one or more other proteins, cell debris, and the like.

DESCRIPTION OF THE PREFERRED EMBODIMENTS

The following description provides details of the manner in which the embodiments of the present invention may be made and used in order to achieve the separation and purification of Factor IX to a degree of purity and concentration not known heretofore to be achievable in one step. This description, while exemplary of the present invention as applied to purification of Factor IX, is not to be construed as specifically limiting the invention and such variations which would be within the purview of one skilled in this art are to be considered to fall within the scope of this invention. The other vitamin K-dependent proteins are purified by the same procedure, modified to the extent of employing another protein of interest instead of Factor IX to grow the antibody that is used.

A. Preparation of Monoclonal Antibody to Factor IX

The monoclonal antibody to Factor IX which is subsequently bound to the separation substrate was prepared in a stepwise procedure starting with a preparation of Factor IX which is highly purified by any of several published methods. The purification can be accomplished with material obtained from a plasma source, or less highly purified material is used in higher concentration.

Purification of anticoagulated normal plasma was performed by the process described by Osterud et al., involving the sequence of $BaSO_4$ adsorption and elution, DEAE-cellulose batch chromatography, polyacrylamide gel electrophoresis, and affinity chromatography on a heparin-agarose column. The sequence of process steps provides highly purified Factor IX.

Mice were injected with highly purified Factor IX obtained from plasma, according to the following schedule. Other schedules may be expected to be equally as effective. On day zero, the mice were injected intraperitioneally with a composition prepared by dissolving (or suspending) 100 μg of the protein in 0.1 ml of buffer containing 0.05 M Tris, 0.15 M sodium chloride, at pH 7.3 and shaking with an equal volume of complete Freund's adjuvant. On day 15, the mice were again injected with 56 μg of the same material except that incomplete Freund's adjuvant was substituted for complete Freund's adjuvant. On days 22, 30. 38 and 124, the injection of day 15 was repeated. On day 239, the mice were injected with purified Factor IX only. On day 243, the spleens of the mice were removed and fused according to a standard procedure, of the type described by J. P. Brown et al, "Protein Antigens of Normal and Malignant Human Cells Identified by Immuno-precipitation with Monoclonal Antibodies," *JOURNAL OF BIOLOGICAL CHEMISTRY*, Vol. 225, pp. 4980–4983 (1980). The standard technique was varied only to the extent that 35% polyethylene glycol 1000 was substituted for 50% polyethylene glycol.

Positive clones were identified by incubating supernatant medium from each clone with an equal part of normal human plasma and assaying for Factor IX activity. Clones were considered positive if the supernatant substantially neutralized Factor IX clotting activity. After determining the clones which were positive they were subcloned at least twice and stable clones producing antibody to Factor IX were then injected into the peritoneal cavities of Balb/C mice which had been pretreated intraperitioneally with 0.5 ml of pristane at least four days prior to injection of cells. Hybridoma cells were injected at concentrations of approximately $5 \times 10^6$ cells per mouse in 0.5 ml of Delbecco's modified Eagle's medium without fetal bovine serum. The mice were tapped when bloated and ascites fluid collected in heparin at approximately 10 units/ml. Ascites fluid from multiple mice were pooled to provide a convenient volume for subsequent isolation of the monoclonal IgG. If the heparinized ascites fluid is not used immediately, it may be stored at $-70°$ C. and thawed just prior to use. The final yield of IgG from the ascites fluid is approximately 1 g of IgG per 100 ml of ascites fluid.

The specificity of the monoclonal IgG for the purpose of purifying Factor IX may be assessed by coupling the IgG to a separation substrate medium, in the manner described hereinafter, and demonstrating that the bound IgG removes Factor IX from plasma and that the Factor IX may be subsequently eluted with a solution containing sodium thiocyanate.

The monoclonal IgG, which is to be used subsequently to prepare the immunoadsorbent, may be isolated from heparinized pooled ascites fluid immediately after collection or a frozen portion of the stored solution may be thawed. Regardless of whether fresh or frozen material is used, the solution was brought to 4° C. and treated with an equal volume of phosphate buffered saline solution (PBS), the composition of which is set forth below. The diluted ascites was precipitated by dropwise addition with stirring at 4° C. of an equal volume of saturated ammonium sulfate (SAS) (prepared by boiling an excess of ammonium sulfate in water, cooling to 4° C., filtering undissolved crystals and adjusting the pH to 7.0 with ammonium hydroxide). The precipitate and its supernatant liquid were stirred for over 2 hours and centrifuged at 4° C. Centrifugations are preferably carried out at 14,000 rpm for 60 minutes (30,000 $\times$ g). The supernatant solution of ascites was precipitated twice more with SAS and the mixture of precipitate and supernatant liquid stirred and centrifuged in the same manner as in the first cycle. The pellets resulting from the third precipitation were resuspended in a volume of PBS equal to that of the diluted ascites fluid and then dialyzed exhaustively against PBS. Clots appearing in the dialysis bags were removed by centrifugation at 20° C. The dialyzed IgG was adsorbed by stirring it with a 5% aqueous solution of aluminum hydroxide at room temperature and centrifuging at 20° C. after adsorption. The adsorption treatment was repeated at least three more times using 2.5% aluminum hydroxide solution for each treatment after the first. The adsorbed IgG was brought to 4° C. and reprecipitated once with SAS as described above. The precipitated pellets may be stored at $-20°$ C. until used. Other methods of purifying the monoclonal IgG may be as good as or better than the method used herein, such as that described in Bruck, C.; Portetelle, D.; Glimeur, C.; and Bollen, A. "One-Step Purification of Mouse Monoclonal Antibodies from Ascitic Fluid by DEAE Affi-gel Blue Chromatography". Journal of Immunological Methods, 53:313-319 (1982).

B. Preparation of the Immunoadsorbent

The immunoadsorbent was prepared by suitably preparing the monoclonal IgG for coupling, preparing the solid substrate for coupling and reacting the two components to bind the former to the latter.

(i) Preparation of IgG for Coupling

Either freshly precipitated IgG may be used or previously frozen precipitate may be thawed for use. The material was then dialyzed against PBS, and while still in the PBS, the volume and IgG concentration ($A_{280}/1.4 = $ mg/ml IgG) determined. The IgG was then treated with between 10 and 30 microliters, preferably 20 microliters, of diisopropylfluorophosphate per 50 ml of IgG solution. The resulting solution was stirred at room temperature in a hood for 30 minutes and the treated IgG, immediately prior to use, was dialyzed overnight against coupling buffer. The coupling buffer found most suitable is a 0.25 M sodium bicarbonate solution adjusted to a pH of 9, preferably with sodium hydroxide.

(ii) Preparation of Solid Substrate for Coupling

Although the monoclonal antibody may be bound to any material which does not have a high affinity for protein, and particularly for Factor IX itself, such materials as glass beads, agarose and derivatives thereof are preferred. Most preferred is a cross-linked agarose available commercially as a gel known as Sepharose 4B (trademark of pharmacia Fine Chemicals, Piscataway, N.J.).

The method of preparing the preferred immunoadsorbent resin is generally the same as that disclosed in the literature, such as the method of J. Porath, et al., Journal Of Chromatography, Vol. 86, pp. 53-56 (1973). The method found most suitable is as follows: a volume of about 2 liters of Sepharose 4B was placed in an acid-cleaned 2 liter sintered glass filter funnel. The resin was washed with water and filtered to a moist cake. The washed resin was placed in a large (approximately 4 liter) glass beaker equipped with a magnetic stirring bar. To the resin was then added 750 ml of cold potassium phosphate buffer solution, prepared by mixing one part of a 5M dibasic potassium solution with two parts of 5M tribasic potassium phosphate colution. Sufficient cold water was added to bring the final volume to 3 liters. The mixture was then chilled to 4° C. and maintained at between 4°-10° C. in an ice water bath placed on a magnetic stirring plate. In a hood, cyanogen bromide was added to 300 ml of water in a stoppered glass bottle containing a magnetic stirring bar. The mixture was rapidly stirred until solution resulted. The cyanogen bromide solution was then added with stirring over a 2 minute period to the cold Sepharose mixture. Stirring was continued for an additional 8 minutes and the solution then transferred to a chilled 2 liter sintered glass filter funnel supported in a 4 liter vacuum flask. The cyanogen bromide treated resin was then washed with approximately 20 liters of cold water (until the pH of the filtrate was neutral). The washed resin was then quickly equilibrated with cold coupling buffer and then transferred to a 4 liter plastic beaker equipped with a large magnetic stirring bar.

(iii) Coupling the Monoclonal Antibody to the Solid Substrate

The solid substrate resin, prepared as indicated above, is ready to be used when it is equilibrated with PBS and should not be stored thereafter. Accordingly, the resin mixture was combined with the IgG which was previously dialyzed overnight against coupling buffer. The combined resin/IgG suspended mixture was stirred at 4° C. for a period of about 24 hours. The $A_{280}$ of an undiluted sample of the supernatant coupling liquid may be determined using bovine serum albumin (BSA) as a standard or Bio-Rad protein assay (Bradford reagent) with BSA as standard. The percentage ligand which is coupled may then be calculated. When the above described procedure is followed, this is usually about 95%. Any remaining active sites on the resin not coupled to antibody may be blocked by washing the resin on a sintered glass filter funnel with cold coupling buffer containing 0.1M glycine. The resin was then resuspended in this solution to a final volume equal to that when the resin and antibody, each in coupling buffer, were combined. The suspension was stirred slowly overnight at 4° C. The resin was then washed thoroughly with PBS, the composition of which is given below. The coupled, blocked resin was then pre-eluted with PBS additionally containing 0.5M calcium ions, preferably calcium chloride. The resin was again washed with PBS alone and stored at 4° C. or in a continuously pumped column at room temperature until ready for use. The coupling density of IgG to SEPHAROSE should be 2-5 g, preferably 3-4 g IgG/liter of SEPHAROSE beads.

C. Separation and Purification of Factor IX

Sample preparations of Factor IX, such as human and animal plasmas and commercial concentrates of Factor IX, may be employed in the present invention and the method is not limited to a particular type of material. Preferred materials, and those which have demonstrated successful results, are human plasmas, plasma fractions, and concentrates, commercially available or partially purified in the laboratory, containing the desired protein. The following description provides details for using normal human plasma.

Plasma, when not freshly drawn, is citrated by conventional means and stored frozen. When ready to be used it is thawed at a temperature of between 35°-40° C., preferably 37° C. and applied directly to the column.

It should be noted that while the description of the present invention refers, and is directed primarily, to the use of immunoadsorbent coupled particles in a chromatography column, it is within the scope of this invention to perform batchwise separations by placing the antibody-bound resin particles in a suitable container, thereafter adding reconstituted concentrate or plasma, and then recovering the desired protein as outlined above and described in more detail below.

When the process is carried out in a chromatography process, the following embodiments are preferred:

The resin was placed in a column, such as an Amicon 86001, (trademark of Amicon Corp., Lexington, Mass.), equipped with a peristaltic pump and a high flow head. When human plasma is used as the source of Factor IX, for every volume of antibody-bearing beads about 3 to 7 and preferably about 5 volumes of plasma are treated. The plasma is poured slowly through the column, at a flow rate which is effective to provide contact time that permits adsorption of the desired amount of the Factor IX from the plasma onto the immunoadsorbent. Longer contact times are preferred, to permit adsorption of at least about 50% of the protein of interest, although it will be recognized that adsorption of at least about 75% is preferable and at least about 95% is even more preferred. A contact time of 1 to 6 hours, preferably 2 to 4 hours, is generally satisfactory.

After the source material was applied to the column, the column was washed with 50 volumes of Tris-lithium chloride buffer (0.1 M lysine base and 0.5 M lithium chloride, pH 8) effective to remove elutable proteins, preferably removing at least 90% and more preferably maximizing their removal. This is followed by a second washing with Tris-hydrochloride buffer (0.05 M Tris-hydrochloride, pH 8) under conditions which are effective to maximize removal of lithium ions from the column. A contact time of about 2-4 hours is satisfactory.

Elution of purified Factor IX is accomplished with buffer containing an eluant such as diethylamine, calcium chloride, sodium thiocyanate, potassium bromide, acetic acid (preferably at a concentration of about 0.1-1.0 M), or a hydrochloric acid-glycine mixture having a pH of 2 to 3, preferably about 2.2. Other suitable eluting agents can readily be identified by those of ordinary skill in this art. Although a linear concentration gradient works well, it is not required in order to accomplish the object of this invention; a solution having a fixed ionic concentration is quite adequate. The flow rate should be effective to elute the protein without raising the column pressure by causing packing of the Sepharose. Thus, when Factor IX is eluted with sodium thiocyanate, an eluant 2M to 4M and preferably 3M in sodium thiocyanate is applied at a flow rate effective to provide a pressure at the inlet of less than 9 pounds per square inch in a 3-liter column, without incurring an increase in pressure. Elution with diethylamine is preformed with a concentration of between 0.3 and 0.7 M, preferably 0.5M. When diethylamine is the eluant, fractions should be collected in 1M glycine to neutralize diethylamine. The column should then be washed with PBS or another neutral buffer.

Fractions containing Factor IX activity are pooled and the total volume and activity of the pool determined. The eluted Factor IX was displayed against PBS to remove ions of the eluant, and then assayed. The eluted Factor IX is present in a concentration of about 10 to about 30 units/ml, and as recovered can be used for therapeutic or analytical applications.

The Factor IX pool can be concentrated to 10-20 ml by a standard procedure such as pressure ultrafiltration. For this purpose, an Amicon stirred cell with a YM-10 membrane under 50 psi of nitrogen pressure has been found to work well. Slow stirring is continued for 30 minutes after nitrogen pressure is released, and the volume and activity of the concentrated pool are determined. The pool may be stored for a brief period, overnight for example, if a temperature of 4° C. is maintained.

The immunoadsorbent column described above is regenerated by elution of the purified protein off of the column. The column can thus be repeatedly used indefinitely.

Assays are performed with a standard partial thromboplastin time assay.

Inclusion of 10 mM tetrasodium EDTA in all buffers, and/or conducting all process steps at 4° C., minimizes activation and proteolysis of Factor IX.

The composition of the buffer solutions is as follows:

Phosphate Buffered Saline Solution:

1.6 g sodium phosphate, monobasic monohydrate
8.4 g sodium phosphate, dibasic anhydrous
61.4 g sodium chloride
Water to 7 liters
pH of buffer is 7.2

In seven different runs using the procedure described above, recovery averaged 52% and ranged from 32% to 71%. Purification averaged 2400-fold, with a specific activity of 34.8 units/mg. The data listed hereinafter in Example I are representative of that obtained according to the present invention, as described above. Frozen normal human plasma was thawed at 37° C., then treated in accordance with the invention at 4° C.

EXAMPLE I

Run A: 100 ml of human plasma, containing 1.5 units/ml and 0.021 units/mg of Factor IX activity, was applied to an immunoadsorbent column, and the plasma and then the Factor IX were eluted, in accordance with the process set forth above. The eluted Factor IX had a specific activity of 31 units/mg, representing an almost 1500-fold purification. Recovery of Factor IX was 63.3%. In the peak eluted fraction, concentration of Factor IX was 12-fold.

Run B: 100 ml of human plasma, containing 0.94 units/ml and 0.013 units/mg of Factor IX activity, was recovered using the above procedure except that all buffers also contained 10 mM of $Na_4$EDTA. The eluted Factor IX had a specific activity of 17 units/mg, representing about a 1300-fold purification. Recovery of Factor IX was 61%. In the peak eluted fraction, concentration of Factor IX was 8-fold.

What is claimed is:

1. A method of recovering an active, highly purified and concentrated vitamin K-dependent protein, from a source comprising a mixture of said vitamin K-dependent protein with one or more other proteins, comprising:
    (a) adsorbing said vitamin K-dependent protein from said source onto particles bound to a monoclonal antibody specific to said vitamin K-dependent protein,
    (b) removing the source depleted in said vitamin K-dependent protein from the particles with an aqueous buffered solution containing lithium chloride, and then
    (c) eluting the adsorbed vitamin K-dependent protein from particles with a buffered eluant.

2. The method of claim 1 wherein said source is plasma, a plasma fraction, or a plasma concentrate.

3. The method of claim 1 wherein said source has been expressed by a cell containing a gene for producing said selected protein.

4. The method of claim 1 wherein said selected protein is Factor IX.

5. The method of claim 2 wherein said selected protein is Factor IX.

6. The method of claim 3 wherein said selected protein is Factor IX.

7. The method according to claim 1, wherein the buffered eluant used in step (c) is sodium thiocyanate in aqueous solution.

8. The method according to claim 1, wherein the buffered eluant used in step (c) is potassium bromide in aqueous solution.

9. The method according to claim 1, wherein the buffered eluant used in step (c) is diethylamine.

10. The method according to claim 1, wherein the buffered eluant used in step (c) is calcium chloride in aqueous solution.

11. The method according to claim 1, wherein said adsorbent particles in step (a) are agarose.

12. The method of claim 1 wherein the buffered eluant used in step (c) is diethylamine or an aqueous solution of a solute selected from the group consisting of calcium chloride, sodium thiocyanate, potassium bromide, acetic acid, and glycine-hydrochloric acid.

13. A method of recovering active, highly purified and concentrated Factor IX, from a source comprising a mixture of Factor IX with one or more other proteins, comprising:
    (a) contacting said source for a period of between 1 to 6 hours with a monoclonal antibody specific to Factor IX which has been coupled to a solid substrate,
    (b) eluting the source depleted in Factor IX from said substrate with an aqueous buffered solution containing lithium chloride, and then
    (c) eluting the adsorbed Factor IX from said substrate with a buffered eluant to recover Factor IX.

* * * * *